United States Patent
Liu et al.

(10) Patent No.: US 12,076,702 B2
(45) Date of Patent: Sep. 3, 2024

(54) DEVICE AND METHOD FOR OXIDIZING ORGANIC SUBSTANCE

(71) Applicant: WANHUA CHEMICAL GROUP CO., LTD., Shandong (CN)

(72) Inventors: Peng Liu, Shandong (CN); Xican Sun, Shandong (CN); Faming Zhu, Shandong (CN); Zhenxia Cong, Shandong (CN); Xiaofei Qiao, Shandong (CN)

(73) Assignee: WANHUA CHEMICAL GROUP CO., LTD., Shandong (CN)

( * ) Notice: Subject to any disclaimer, the term of this patent is extended or adjusted under 35 U.S.C. 154(b) by 546 days.

(21) Appl. No.: 17/288,708

(22) PCT Filed: May 10, 2019

(86) PCT No.: PCT/CN2019/086440
§ 371 (c)(1),
(2) Date: Apr. 26, 2021

(87) PCT Pub. No.: WO2020/133872
PCT Pub. Date: Jul. 2, 2020

(65) Prior Publication Data
US 2021/0402363 A1     Dec. 30, 2021

(30) Foreign Application Priority Data
Dec. 26, 2018    (CN) ................... 201811603256.6

(51) Int. Cl.
*B01J 19/24*     (2006.01)
*B01J 19/00*     (2006.01)
*C07C 407/00*    (2006.01)

(52) U.S. Cl.
CPC ......... *B01J 19/245* (2013.01); *B01J 19/0053* (2013.01); *B01J 19/006* (2013.01); *C07C 407/00* (2013.01); *B01J 2219/0004* (2013.01)

(58) Field of Classification Search
USPC .................................................. 568/561, 571
See application file for complete search history.

(56) References Cited

U.S. PATENT DOCUMENTS

| 4,066,706 A | 1/1978 | Schmidt |
| 4,262,143 A | 4/1981 | Becker |

FOREIGN PATENT DOCUMENTS

| CN | 1023894 C    | 3/1994 |
| CN | 101022885 A  | 8/2007 |

(Continued)

OTHER PUBLICATIONS

Machine translation of Patent No. CN101704742A, May 5, 2010; pp. 1-8 (Year: 2010).*

(Continued)

*Primary Examiner* — Medhanit W Bahta
(74) *Attorney, Agent, or Firm* — Norton Rose Fulbright US LLP; James R. Crawford

(57) ABSTRACT

Disclosed are a device and method for oxidizing an organic substance, particularly a method for preparing ethylbenzene hydroperoxide by reacting ethylbenzene with an oxygen-containing gas. The device comprises a vertical bubbling reactor (1) and a horizontal bubbling reactor (11) connected to a reaction product outlet of the vertical bubbling reactor (1), wherein the horizontal bubbling reactor (11) is internally provided with a plurality of reaction compartments (21) which are arranged along the axial direction thereof, and a liquid phase channel (22) is provided between adjacent reaction compartments (21).

3 Claims, 1 Drawing Sheet

(56) References Cited

FOREIGN PATENT DOCUMENTS

| | | | | |
|---|---|---|---|---|
| CN | 101704742 A | | 5/2010 | |
| CN | 104815593 A | | 8/2015 | |
| CN | 106554298 A | * | 4/2017 | |
| CN | 107930555 A | * | 4/2018 | .......... B01J 19/0053 |
| CN | 109020858 A | | 12/2018 | |
| JP | H0672911 A | | 3/1994 | |
| JP | H06285364 A | | 10/1994 | |
| KR | 20160089393 A | | 7/2016 | |
| WO | 2006024655 A1 | | 3/2006 | |
| WO | 2008058925 A1 | | 5/2008 | |
| WO | 2009024549 A3 | | 4/2009 | |
| WO | 2011100830 A1 | | 8/2011 | |

OTHER PUBLICATIONS

Machine translation of CN107930555A, Apr. 5, 2017; pp. 1-12 (Year: 2017).*
Machine translation of CN106554298A, Apr. 20, 2018; pp. 1-17 (Year: 2018).*
International Search Report in connection with PCT Application No. PCT/CN2019/086440.
Office Action issued on Sep. 28, 2020 by the CIPO in the corresponding Patent Application No. 201910391553.7, with English translation.
European Search Report issued on Jun. 27, 2022 in corresponding patent application No. 19904824.0-1101.
Office Action issued on May 19, 2022 by the JPO in the corresponding Patent Application No. 2021-519772, with English translation.
Office Action issued on Sep. 16, 2022 by the KIPO in the corresponding Patent Application No. 10-2021-7011097, with English translation.

* cited by examiner

DEVICE AND METHOD FOR OXIDIZING ORGANIC SUBSTANCE

This application is a national phase under 35 U.S.C. § 371 of International Application No. PCT/CN2019/086440 filed on May 10, 2019, which claims the benefit of priority from Chinese Patent Application No. 201811603256.6 filed on Dec. 26, 2018. The entire contents of these applications are incorporated herein by reference in their entirety.

TECHNICAL FIELD

The present disclosure relates to a method for oxidizing an organic substance such as ethylbenzene or cumene or cyclohexane and, in particular, to a method for preparing ethylbenzene hydroperoxide by contacting and reacting ethylbenzene with an oxygen-containing gas.

BACKGROUND

The coproduction of propylene oxide (PO) and styrene (SM) (i.e., PO/SM method) is one of the best processes for producing PO at present. The PO/SM method mainly includes three steps: (1) contacting and oxidizing ethylbenzene with air to produce ethylbenzene hydroperoxide (EBHP); (2) oxidizing propylene by EBHP into propylene oxide, where EBHP is reduced to phenyl methyl alcohol; (3) dehydrating phenyl methyl alcohol to produce styrene. The reaction route may be represented by Formula (1):

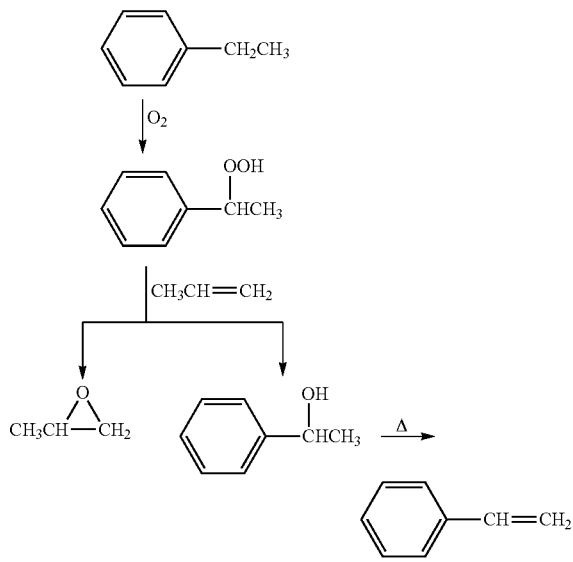

The oxidation of ethylbenzene to ethylbenzene hydroperoxide is the key to the PO/SM method. While ethylbenzene is oxidized to EBHP, EBHP is further subjected to a series of side reactions, resulting in a decrease in the selectivity of EBHP. Therefore, the single pass conversion of ethylbenzene in industrial processes is generally lower than 10%.

At present, an ethylbenzene oxidation reactor used in industry is generally a horizontal bubble column reactor. U.S. Pat. Nos. 4,066,706 and 4,262,143 have disclosed a horizontal reactor. The reactor is divided into 5 to 10 zones by baffles, an ethylbenzene reaction liquid enters the reactor from one side and is discharged from the other side after passing through these zones in sequence, and air is bubbled from the bottom into the corresponding zones and is discharged from the top after being in contact with ethylbenzene.

The above reactor is widely used in peroxidation of organic substances, with the problem of insufficient gas-liquid contact. Shell has publicly reported (Chemical Engineering Science, 62(2007)5495-5502) a lack of oxygen in some areas of such reactors, resulting in reduced productivity of equipment.

In addition, the oxidation process of an organic substance generally follows the mechanism of free radicals and requires a certain initiation time at an initial reaction stage. During a normal operation of the horizontal reactor, most of the fluid flows in a horizontal direction and the back-mixing of a liquid phase is relatively low. This feature is beneficial to the improvement of reaction selectivity but leads to a low reaction rate and a long initiation time at the initial reaction stage, reducing an equipment capacity.

In view of the technical problem of the above horizontal reactor, it is necessary to provide a novel reaction system that improves the performance of the ethylbenzene oxidation reactor, to avoid the related problems of the existing horizontal reactor.

SUMMARY

An object of the present disclosure is to provide a device and method for oxidizing an organic substance and, in particular, provide a device and method for contacting and reacting liquid ethylbenzene with an oxygen-containing gas.

To achieve one aspect of the preceding object, the present disclosure provides technical solutions described below.

A device for oxidizing an organic substance includes a vertical bubble reactor and a horizontal bubble reactor, where the horizontal bubble reactor is connected to a reaction product outlet of the vertical bubble reactor and internally provided with a plurality of reaction compartments arranged in the axial direction of the horizontal bubble reactor, and a liquid phase channel is provided between adjacent reaction compartments.

The present disclosure is implemented by a combination of the vertical bubble reactor and the horizontal bubble reactor, and the included vertical bubble reactor should be construed as being substantially perpendicular to a horizontal plane. The vertical bubble reactor includes a liquid inlet and a gas inlet arranged at the lower portion of the reactor and a liquid outlet and a gas outlet arranged at the upper portion of the reactor, for example, a liquid outlet disposed on a side surface of the upper portion of the reactor and a gas outlet disposed at the top of the reactor; and the vertical bubble reactor is internally provided with a flow guide cylinder along a longitudinal direction, where the flow guide cylinder allows a fluid to pass through. In an embodiment, the flow guide cylinder is preferably disposed at a position such that the centerline of the flow guide cylinder coincides with the axis of the vertical bubble reactor. The flow guide cylinder may have various shapes, for example, the flow guide cylinder may have a circular, rectangular, square, or elliptical cross-section. Preferably, the flow guide cylinder is a tubular flow guide cylinder with a circular cross-section.

According to the device of the present disclosure, in an embodiment, the height of the flow guide cylinder is 10-90%, preferably 20-80%, more preferably 40-70% (for example, 50% or 60%) of the height of the vertical bubble reactor; and the cross-sectional area of the flow guide cylinder is 5-60%, preferably 10-25% (for example, 15%, 20%, or 40%) of the cross-sectional area of the reactor.

According to the device of the present disclosure, in an embodiment, the vertical bubble reactor is further internally provided with a first gas distributor connected to the gas inlet, where the first gas distributor has distribution holes that are distributed inside the flow guide cylinder or an annular gap between the flow guide cylinder and the inner wall of the reactor. Such an arrangement manner of the distribution holes can make a gas holdup in the flow guide cylinder significantly different from a gas holdup in the annular gap between the flow guide cylinder and the inner wall of the reactor, so that the resulting difference in fluid density between two regions can cause the fluid to circulate in these two regions, which facilitates the enhancement of liquid back-mixing in the vertical bubble reactor and a decrease in an initiation time of a reaction. The gas distributor may be in any form well-known to those skilled in the art, such as a ring distributor and a branched pipe distributor.

According to the device of the present disclosure, in an embodiment, the inner wall of the vertical bubble reactor is provided with a vertical reactor outlet overflow weir located at the liquid outlet, and the upper end of the flow guide cylinder is lower than the vertical reactor outlet overflow weir.

The horizontal bubble reactor should be construed as being substantially parallel to the horizontal plane. The horizontal bubble reactor is provided with a reaction liquid inlet and a reaction liquid outlet at two ends in the axial direction, respectively, and each of the plurality of reaction compartments is provided with a reaction gas inlet at the lower end, a reaction gas outlet at the upper end, and a second gas distributor connected to the reaction gas inlet inside. The second gas distributor may generally be a porous tube, where the openings have a pore size of 1-15 mm, preferably 2-6 mm, and the porosity is optionally 0.01-10%, preferably 0.02-3%, for example, 1% or 2%. When a single reaction compartment is internally provided with a plurality of porous tubes for gas distribution, the porous tubes may be uniformly distributed on the same horizontal plane at the bottom of the reactor or uniformly distributed along the arc of the bottom of the reactor, preferably uniformly distributed along the arc of the bottom of the reactor.

The plurality of reaction compartments are separated by partition plates arranged inside the horizontal bubble reactor, and the liquid phase channel is a liquid phase channel disposed on the partition plates, preferably a liquid phase channel disposed at the bottom of the partition plates. The liquid phase channel can avoid the liquid flow dead zone that easily appears at the bottom of the reactor to promote the peroxidation reaction for preparing ethylbenzene hydroperoxide. It is appreciated by those skilled in the art that the shape of the liquid phase channel may be circular, rectangular, arc-shaped, or any other shape, preferably circular.

According to the device of the present disclosure, in an embodiment, each of the plurality of reaction compartments is internally provided with at least one vertical baffle arranged along a liquid flow direction in a normal operation, where the bottom of the baffle is not higher than the gas distributor of the reaction compartment where the baffle is located. For example, each reaction compartment includes two vertical baffles arranged along the liquid flow direction in the normal operation, and the baffles have flow guide plates. In the normal operation, a liquid flows from one end of the horizontal bubble reactor to the other end of the horizontal bubble reactor so that the baffles are arranged along a direction from one end to the other end of the reactor.

The two baffles are symmetrically arranged with respect to the centerline of the horizontal bubble reactor. In an embodiment, the baffle is further provided with a plurality of openings, the bottom of the baffle has a distance not smaller than 50 mm from the inner wall of the horizontal bubble reactor, and the height of the baffle is 10-70%, more preferably 20-50% (for example, 30% or 40%) of the height of the horizontal bubble reactor.

According to the device of the present disclosure, in an embodiment, the side surface of the baffle is provided with a plurality of flow guide plates inclined downwards. In an embodiment, the ratio of the sum of areas of the plurality of flow guide plates to the area of the baffle is 0.01-0.15, preferably 0.05-0.1. In an embodiment, each of the plurality of flow guide plates is tongue-shaped.

According to the device of the present disclosure, in an embodiment, the vertical bubble reactor and the horizontal bubble reactor may each have a sufficient gas phase space to avoid the entrainment of peroxide with a gas phase into other equipment. The height of the gas phase space should not be lower than 0.5 m, for example, 0.8 m, 1 m or 1.2 m. The height of the gas phase space refers to a distance between the gas outlet of the reactor and a lower liquid level.

According to the device of the present disclosure, in an embodiment, other spare liquid outlets are arranged at different heights of the vertical bubble reactor, respectively. These spare liquid outlets may be opened when necessary, to control the liquid level and adjust reaction residence time.

According to the device of the present disclosure, in an embodiment, the device for oxidizing an organic substance of the present disclosure further includes a liquid distributor, where the liquid distributor is disposed at the lower portion of the vertical bubble reactor (for example, below the flow guide cylinder) and configured to uniformly distribute the raw material(s) introduced from the liquid inlet.

To achieve another aspect of the preceding object, the present disclosure provides the following technical solution: the preceding device is used for preparing ethylbenzene hydroperoxide by contacting ethylbenzene with an oxygen-containing gas.

According to the method of the present disclosure, when ethylbenzene hydroperoxide is prepared by contacting ethylbenzene with the oxygen-containing gas, liquid ethylbenzene enters a vertical bubble column reactor from the lower portion thereof, the oxygen-containing gas also enters the vertical bubble column reactor from the lower portion thereof and is dispersed into the reaction liquid through a gas distributor, and liquid ethylbenzene and the oxygen-containing gas pass through a vertical bubble reactor in parallel, during which ethylbenzene contacts and reacts with the oxygen-containing gas so that ethylbenzene hydroperoxide is produced. A gas phase is discharged from the top of the reactor and a liquid reaction product flows out of the vertical reactor through a vertical reactor outlet overflow weir at the upper portion of the reactor.

According to the method of the present disclosure, the liquid reaction product flowing out of the vertical bubble reactor enters a horizontal bubble reactor from one end of the horizontal bubble reactor, the oxygen-containing gas is dispersed into the liquid reaction product from the bottom of the horizontal bubble reactor through a second gas distributor, the liquid reaction product and the oxygen-containing gas flow across each other in the horizontal bubble reactor, during which ethylbenzene continues to contact and react with the oxygen-containing gas so that ethylbenzene hydroperoxide is produced. A gas phase is discharged from the top of the horizontal bubble reactor and mixed with the gas phase from the vertical bubble reactor, and then enters a subsequent ethylbenzene recovery step, and the liquid reaction product is discharged from the other end of the horizontal bubble reactor, and then enters a subsequent step.

Generally, a plurality of partition plates are spaced apart along a longitudinal direction in the horizontal bubble reactor so as to divide the horizontal bubble reactor into a plurality of independent reaction compartments that are arranged laterally. A liquid phase channel is disposed between adjacent reaction compartments so that the fluid can pass from one compartment to another for a continual reaction. These independent reaction compartments may be operated under different conditions such as different reaction temperatures or different flow rates of the oxygen-containing gas.

According to the method of the present disclosure, the arrangement of a vertical bubble column and a flow guide cylinder inside can enhance the back-mixing of a liquid phase, increase the concentration of free radicals in the reaction system, greatly reduce the effect of a wall effect on the annihilation of free radicals, reduce an initiation time of the reaction, reduce the production of by-products at an initiation stage, and improve the selectivity of EBHP. However, due to a series of side reactions in the peroxidation process of ethylbenzene, too high a concentration of EBHP also leads to a decrease in the selectivity of EBHP. Therefore, to obtain optimal product selectivity, the concentration of ethylbenzene hydroperoxide at the initiation stage of the reaction, that is, the concentration of ethylbenzene hydroperoxide at the outlet of the vertical bubble reactor, should be controlled. In an embodiment, the concentration of ethylbenzene hydroperoxide at the outlet of the vertical bubble reactor may be controlled at 0.5%-1.5%, preferably 1%-1.5%, for example, 0.6%, 0.8%, 0.9%, 1.2%, 1.3%, or 1.4%.

In an embodiment, if the horizontal bubble reactor includes N reaction compartments (i.e., reaction compartments actually used in the horizontal bubble reactor) and ethylbenzene hydroperoxide has a concentration of C at the outlet of the reaction system, the concentration of ethylbenzene hydroperoxide at the outlet of the vertical bubble reactor should be controlled at 80%-95% of $$\frac{C}{N+1}.$$

According to the present disclosure, the vertical bubble reactor containing the flow guide cylinder cooperates with the horizontal bubble reactor containing rectifying baffles and multiple compartments so that the initiation stage of an oxidation reaction of ethylbenzene is carried out under a strong back-mixing condition and a conventional reaction stage is carried out under the conditions of a gradually decreased temperature and weak back-mixing, and the concentration of ethylbenzene hydroperoxide in the strong back-mixing portion, that is, the vertical bubble reactor, is strictly controlled, thereby constructing an efficient production method conforming to ethylbenzene oxidation reaction characteristics and improving reaction efficiency and selectivity.

Figure 1:
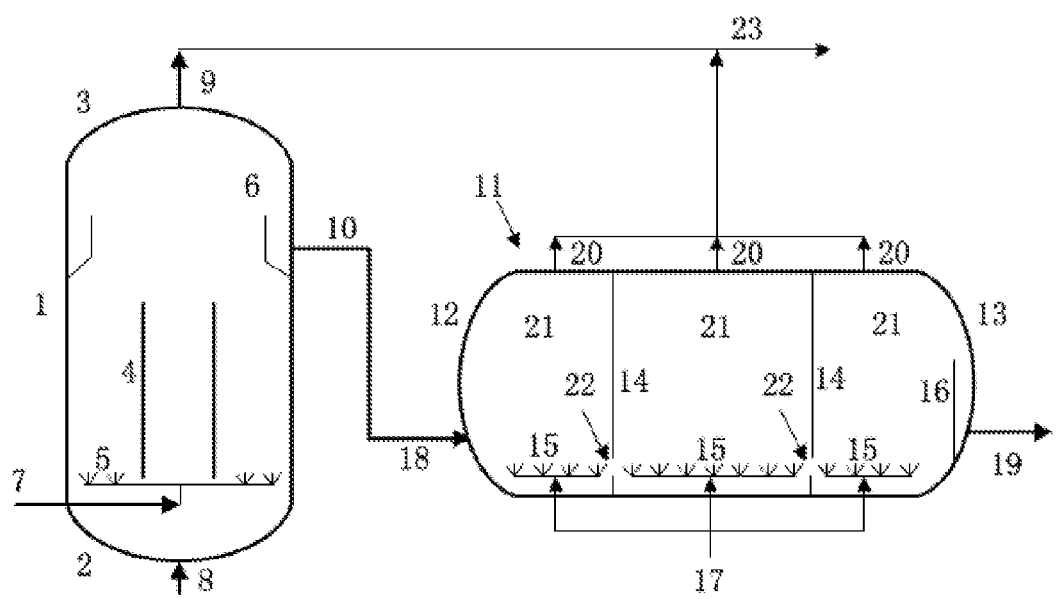
FIG. 1 is a schematic diagram of an embodiment of a method for preparing ethylbenzene hydroperoxide by contacting ethylbenzene with an oxygen-containing gas.

REFERENCE LIST 1 vertical bubble reactor
2 lower head
3 upper head
4 flow guide cylinder
5 first gas distributor
6 vertical reactor outlet overflow weir
7 gas inlet of the vertical reactor
8 liquid inlet of the vertical reactor
9 gas phase outlet of the vertical reactor
10 liquid outlet of the vertical reactor
11 horizontal bubble reactor
12 left head
13 right head
14 partition plate
15 second gas distributor
16 horizontal reactor outlet overflow weir
17 reaction gas inlet
18 reaction liquid inlet
19 reaction liquid outlet
20 reaction gas outlet
21 reaction compartment
22 liquid phase channel
23 gas phase main pipe
24 baffle
25 flow guide plate

DETAILED DESCRIPTION

Hereinafter the present disclosure will be further described in detail in conjunction with drawings and examples. The examples described below should not be construed as limiting the scope of the present disclosure. Various alterations or changes made according to ordinary technical knowledge and conventional means in the art without departing from the concept of the preceding method of the present disclosure are intended to fall within the scope of the present disclosure.

As shown in FIG. 1, a device for oxidizing an organic substance of the present disclosure includes a vertical bubble reactor 1 and a horizontal bubble reactor 11, where the horizontal bubble reactor 11 is connected to a reaction product outlet of the vertical bubble reactor 1 and internally provided with a plurality of reaction compartments 21 arranged in the axial direction of the horizontal bubble reactor 11, and a liquid phase channel 22 is provided between adjacent reaction compartments 21. The present disclosure is implemented by a combination of the vertical bubble reactor 1 and the horizontal bubble reactor 11. The initiation of a reaction is completed in the vertical bubble reactor 1 and a conventional reaction stage is carried out in the horizontal bubble reactor 11.

The vertical bubble reactor is disposed substantially perpendicular to a horizontal plane and includes a liquid inlet 8 and a gas inlet 7 disposed on a lower head 2 of the reactor and a liquid outlet 10 (i.e. the reaction product outlet) disposed on a side surface of the upper portion of the reactor and a gas phase outlet 9 disposed at the top of the reactor.

The vertical bubble reactor 1 is internally provided with a flow guide cylinder 4 along a longitudinal direction, where the flow guide cylinder 4 allows a fluid to pass through and is preferably disposed along a liquid flow direction of the vertical bubble reactor 1 in a normal operation. In the normal operation, the liquid flow direction of the vertical bubble reactor 1 is from the lower liquid inlet 8 to the upper liquid outlet 10. Therefore, the flow guide cylinder 4 is disposed from the lower portion to the upper portion of the vertical bubble reactor 1. In addition, other spare liquid outlets are arranged at different heights of the vertical bubble reactor 1, respectively. These spare liquid outlets may be opened when necessary, to control a liquid level and adjust reaction residence time. In an example, the flow guide cylinder 4 is preferably disposed at a position such that the centerline of the flow guide cylinder 4 coincides with the axis of the vertical bubble reactor 1. In an example, the device for oxidizing an organic substance of the present disclosure further includes a liquid distributor (not shown in the figure), where the liquid distributor is disposed at the lower portion of the vertical bubble reactor (for example, below the flow guide cylinder 4) and configured to uniformly distribute the raw material(s) introduced from the liquid inlet 8.

The flow guide cylinder 4 may have various shapes, for example, the flow guide cylinder 4 may have a circular, rectangular, square, or elliptical cross-section. Preferably, the flow guide cylinder 4 is a tubular flow guide cylinder with a circular cross-section.

The height of the flow guide cylinder 4 may vary within a relatively wide range. Generally, the height of the flow guide cylinder 4 may be 10-90%, preferably 20-80%, more preferably 40-70% of the height of the vertical bubble reactor 1. The cross-sectional area of the flow guide cylinder 4 may also vary within a relatively wide range. Generally, the cross-sectional area of the flow guide cylinder 4 may be 5-60%, preferably 10-25% of the cross-sectional area of the reactor 1.

A vertical reactor outlet overflow weir 6 is provided on the inner wall of the vertical bubble reactor 1 and fixed to the liquid outlet on the inner wall of the reactor. It is appreciated by those skilled in the art that the lower end of the vertical reactor outlet overflow weir 6 should be lower than the liquid outlet and the upper end of the vertical reactor outlet weir 6 should be higher than the liquid outlet to form an overflow, and the upper end of the flow guide cylinder is lower than the upper end of the vertical reactor outlet overflow weir 6.

The vertical bubble reactor 1 is further internally provided with a first gas distributor 5 connected to the gas inlet 7, where an oxygen-containing gas enters from the lower portion of the vertical bubble reactor 1 and is dispersed into a liquid reactant through the first gas distributor 5. The first gas distributor 5 may be in a form well-known to those skilled in the art, such as a ring distributor and a branched pipe distributor.

All distribution holes of the first gas distributor 5 are arranged inside the flow guide cylinder 4 or an annular gap between the flow guide cylinder 4 and the inner wall of the vertical bubble reactor 1, preferably the latter. Such an arrangement manner of the distribution holes can make a gas holdup in the flow guide cylinder 4 significantly different from a gas holdup in the annular gap between the flow guide cylinder 4 and the inner wall of the reactor, so that the resulting difference in fluid density between two regions can cause the fluid to circulate in these two regions, which facilitates the enhancement of liquid back-mixing in the vertical bubble reactor 1 and a decrease in an initiation time of a reaction.

The openings of the first gas distributor 5 optionally have a pore size of 1-15 mm, preferably 2-6 mm, for example, 3 mm, 4 mm, or 5 mm. The porosity of the first gas distributor 5 is optionally 0.01-10%, preferably 0.02-3%, for example, 1%, 2%, or 2.5%.

The horizontal bubble reactor 11 has a horizontal cylindrical structure and is disposed substantially parallel to the horizontal plane. The horizontal bubble reactor 11 includes a reaction liquid inlet 18 disposed on a left head 12 of the reactor, a reaction liquid outlet 19 disposed on a right head 13 of the reactor, a reaction gas inlet 17 disposed at the bottom of the reactor, a reaction gas outlet 20 disposed at the top of the reactor, and a plurality of reaction compartments 21, where a horizontal reactor outlet overflow weir 16 may be disposed at the reaction liquid outlet 19 in the last reaction compartment along a liquid flow direction. Generally, a plurality of partition plates 14 are spaced apart along the longitudinal direction in the horizontal bubble reactor 11 so as to divide the horizontal bubble reactor 11 into a plurality of independent reaction compartments 21 that are arranged laterally. A liquid phase channel 22 is disposed between adjacent reaction compartments 21 so that the fluid can pass from one reaction compartment to another for a continual reaction. These independent reaction compartments 21 may operate under different conditions (such as different reaction temperatures or different flow rates of the oxygen-containing gas) through the adjustment of the temperature and composition of introduced gas.

It is appreciated by those skilled in the art that the horizontal bubble reactor 11 including the plurality of reaction compartments 21 may also be equivalent to a plurality of horizontal bubble reactors 11 including one or several reaction compartments 21, to ensure a total volume of the reaction compartments 21.

The liquid phase channel 22 is a liquid phase channel disposed on the partition plate 14, for example, a liquid phase overflow channel disposed at the top of the partition plate 14 and/or a liquid phase communication channel disposed at the bottom of the partition plate 14. Particularly preferably, the liquid phase channel 22 is the liquid phase communication channel disposed at the bottom of the partition plate 14, which can avoid a liquid flow dead zone easily occurring at the bottom of the reactor and promote a peroxidation reaction for preparing ethylbenzene hydroperoxide. It is appreciated by those skilled in the art that the shape of the liquid phase channel 22 may be circular, rectangular, arc-shaped, or any other shape, preferably circular.

The cross-sectional area of the liquid phase channel 22 is generally 0.5%-10%, preferably 1-5% (for example, 2%, 3%, or 4%) of the cross-sectional area of the horizontal bubble reactor 11.

A second gas distributor 15 is provided at the bottom of each reaction compartment of the horizontal bubble reactor 11. The second gas distributor 15 is generally a porous tubular gas distributor. The openings of the second gas distributor 15 optionally have a pore size of 1-15 mm, preferably 2-6 mm, for example, 3 mm, 4 mm, or 5 mm. The porosity of the second gas distributor 5 is optionally 0.01-10%, preferably 0.02-3%, for example, 1%, 2%, or 2.5%.

As described herein, the horizontal bubble reactor 11 includes the plurality of independent reaction compartments 21. In this case, each reaction compartment 21 should include an independent gas inlet 17 and an independent distribution means (the second gas distributor 15), that is, at least one porous tube for gas distribution should be included on each side of each partition plate 14. It is appreciated by those skilled in the art that the number of required porous tubes for gas distribution depends on the size of the gas flow rate and further process conditions.

In the present disclosure, when the second gas distributor 15 in the reaction compartment 21 includes a plurality of porous tubes for gas distribution, the porous tubes may be uniformly distributed on the same horizontal plane at the bottom of the horizontal bubble reactor 11 or uniformly distributed along the arc of the bottom of the reactor, preferably uniformly distributed along the arc of the bottom of the reactor.

Each reaction compartment 21 in the horizontal bubble reactor 11 includes two vertical baffles 24 along the liquid flow direction in the normal operation. Preferably, the two baffles 24 are arranged along the axial direction of the horizontal bubble reactor 11. In the normal operation, the liquid flows from one end of the horizontal bubble reactor 11 to the other end of the horizontal bubble reactor 11 so that the baffles 24 are arranged along a direction from one end to the other end of the reactor. The two baffles 24 are arranged symmetrically with respect to the central axis of the horizontal bubble reactor 11. Each baffle 24 is provided with a plurality of openings, for example, two, four, or eight openings. The porosity of the baffle 24 is 3%~8%, for example, 5%. The side surface of each baffle is provided with two flow guide plates 25 inclined downwards at the openings of each baffle, where an inclination angle (an included angle with the baffle) may be 15-60°, such as 30° or 45°.

The baffle 24 can significantly improve a wall-trending phenomenon of gas in a horizontal reactor, can greatly reduce the back-mixing of gas and avoid the formation of an oxygen-depleted zone in the center of the reactor. This arrangement can effectively reduce the decomposition of ethylbenzene hydroperoxide and improve reaction selectivity. The flow guide plates 25 on the baffle 24 can facilitate the mixing of fluids on two sides of the baffle, ensuring uniform liquid temperature and concentration within the reactor compartment while avoiding the back-mixing of gas.

The height of the baffle 24 may vary within a relatively wide range. Generally, the height of the baffle 24 is 10-70%, preferably 20-50%, for example, 40% of the diameter of the reactor. The bottom of the baffle 24 should not be higher than an adjacent porous tube for gas distribution and has a distance not smaller than 50 mm (such as 80 mm or 100 mm) from the inner wall of the horizontal bubble reactor.

The flow guide plate 25 of the baffle 24 has a tongue-shaped structure. In an example, the ratio of the liquid flow cross-sectional area of the flow guide plates to the cross-sectional area of the baffle is 0.01-0.15, preferably 0.05-0.1.

A certain height difference may exist between the vertical bubble reactor and the horizontal bubble reactor, to ensure that the liquid at the outlet of the vertical reactor can flow into the horizontal reactor by gravity. The vertical bubble reactor and the horizontal bubble reactor may each have a sufficient gas phase space to avoid the entrainment of peroxides with a gas phase into other equipment. The height of the gas phase space should not be lower than 0.5 m, for example, 0.8 m, 1 m or 1.2 m. The height of the gas phase space refers to a distance between the gas outlet of the reactor and a lower liquid level.

During the peroxidation reaction of ethylbenzene, liquid ethylbenzene enters the reactor 1 through the liquid inlet 8 at the lower portion of the vertical bubble column reactor 1, the oxygen-containing gas enters the reactor 1 through the gas inlet 7 at the lower portion of the vertical bubble column reactor 1 and is dispersed into a reaction liquid through the first gas distributor 5, and liquid ethylbenzene and the oxygen-containing gas flow through the vertical bubble reactor 1 in parallel, during which ethylbenzene contacts and reacts with the oxygen-containing gas so that ethylbenzene hydroperoxide is produced. A gas phase substance is discharged from the gas phase outlet 9 at the top of the reactor and the liquid reaction product flows out of the vertical bubble reactor 1 through the liquid outlet 10 after preliminary degassing through the overflow weir 6 at the upper portion of the reactor. The difference in gas holdup inside and outside the flow guide cylinder 4 can promote the mixing of liquids in the reactor, increase the content of free radicals at the lower portion of the reactor, and shorten an initiation time of the reaction.

The liquid reaction product flowing out of the vertical bubble reactor 1 enters the horizontal bubble reactor 11 from the reaction liquid inlet 18 at one end of the horizontal bubble reactor 11, the oxygen-containing gas enters from the reaction gas inlet 17 at the bottom of the horizontal bubble reactor and is dispersed into the liquid reaction product through the second gas distributor 15, the liquid reaction product and the oxygen-containing gas flow across each other in the horizontal bubble reactor 11, during which ethylbenzene continues to contact and react with the oxygen-containing gas so that ethylbenzene hydroperoxide is produced. A gas phase is discharged from the reaction gas outlet 20 at the top of the horizontal bubble reactor 11 and mixed with the gas phase from the vertical bubble reactor 1 and then enters a subsequent ethylbenzene recovery step through a gas phase main pipe 23 and the liquid reaction product is discharged from the liquid outlet 19 at the other end of the horizontal bubble reactor 11 through the horizontal reactor outlet overflow weir 16 and then enters a subsequent step.

To achieve optimal product selectivity, the concentration of ethylbenzene hydroperoxide at the initiation stage of the reaction, that is, the concentration of ethylbenzene hydroperoxide at the outlet of the vertical bubble reactor, should be controlled. For example, the concentration is adjusted by controlling the temperature and/or volume of the introduced gas. In an embodiment, the concentration of ethylbenzene hydroperoxide at the outlet of the vertical bubble reactor may be controlled at 0.5%-1.5%, preferably 1%-1.5%, for example, 0.6%, 0.8%, 0.9%, 1.2%, 1.3%, or 1.4%. Alternatively, in an embodiment, if the horizontal bubble reactor includes N reaction compartments and ethylbenzene hydroperoxide has a concentration of C at the outlet of the reaction system, the concentration of ethylbenzene hydroperoxide at the outlet of the vertical bubble reactor should be controlled at 80%-95% of $$\frac{C}{N+1},$$

for example, 82%, 85%, 88%, 90%, or 92%.

During the reaction, the temperature at which liquid ethylbenzene reacts with the oxygen-containing gas is generally 100-220° C., preferably 120-160° C., for example, 130° C., 140° C., or 150° C. The reaction rate is too low at a temperature below 120° C. The reaction rate of a side reaction is significantly accelerated at a temperature higher than 160° C., reducing the selectivity of ethylbenzene hydroperoxide. To further improve the selectivity of hydroperoxide, the peroxidation reaction may be carried out by decreasing the temperature step by step, thereby minimizing the production of by-products. Therefore, the temperature of the peroxidation reaction may be controlled at 150-160° C. at the initial stage of the reaction, that is, the temperature of the vertical bubble reactor may be controlled at 150-160° C., and then the reaction temperature may be gradually decreased to 120-150° C. such as 130° C. or 140° C. at the later stage, that is, the temperatures of different reaction compartments in the horizontal bubble reactor may be controlled to gradually decrease in the liquid flow direction. Preferably, the temperature difference between adjacent reaction compartments is 1-3° C. The pressure under which ethylbenzene reacts with the oxygen-containing gas is not a critical factor in the process and is generally 1-8 barG.

The present disclosure is further described below in conjunction with examples.

Example 1

Figure 2:
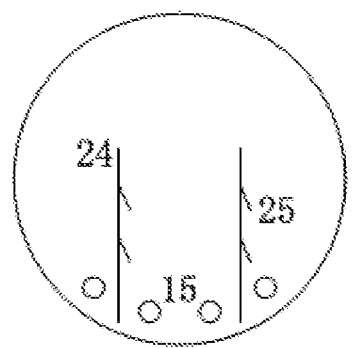
FIG. 2 is a schematic diagram of an embodiment of a flow guide plate in a horizontal bubble reactor.

The device shown in FIG. 1 is used. The vertical bubble reactor 1 has a diameter of about 0.8 m and a total height of about 3 m. The flow guide cylinder 4 has a diameter of 0.3 m and a height of 1.2 m. The gas distributor 5 is a ring tube-shaped gas distributor and has distribution holes arranged between the flow guide cylinder and the inner wall of the reactor, where the openings have a pore size of 2 mm and the porosity is 0.02%. The horizontal bubble reactor 11 has a diameter of about 1.6 m and a length of about 3.66 m. The reactor is divided into four reaction compartments 21 by using three partition plates 14 and a liquid flow channel 22 with a diameter of 100 mm is provided at the bottom of the partition plate 14. Each compartment 21 contains four porous tubes for gas distribution which are uniformly and symmetrically distributed along the arc of the lower portion of the reactor, with an opening diameter of 2 mm and a porosity of 0.05%. As shown in FIG. 2, two vertical baffles that are symmetrical are arranged on inner sides of outermost two porous tubes for gas distribution, where the height of the baffle is 30% of the diameter of the horizontal bubble reactor and the bottom of the baffle has a distance of 50 mm from the inner wall of the reactor. Each baffle is provided with eight rectangular liquid flow openings (a porosity of 5%).

In an operation of this example, a reactant, that is, the liquid discharge from the vertical bubble reactor, bypassed a first compartment of the horizontal bubble reactor, that is, directly entered a second compartment of the horizontal bubble reactor. An ethylbenzene reaction liquid containing 0.02 wt % of ethylbenzene hydroperoxide was added to the above reactor through the liquid inlet 8 at a flow rate of 1.6 tons/hour and flowed through the vertical bubble reactor 1 and the second reaction compartment to the fourth reaction compartment of the horizontal bubble reactor 11 in sequence, while a gas with an oxygen content of about 15 wt % (a mixture of oxygen and nitrogen) was introduced to the reactor through gas inlets 7 and 17 at a total gas flow rate of about 300 kg/h. The reactors were both controlled to operate at a temperature of 138° C. and the gas phase spaces in the reactors had a pressure of about 3.5 barG.

Under the preceding conditions, a reaction liquid mixture with an ethylbenzene hydroperoxide content of about 7.5 wt % can be obtained at the liquid phase outlet of the reactor. The concentration of ethylbenzene hydroperoxide at the outlet of the vertical bubble reactor is about 1.39% and the total selectivity of ethylbenzene hydroperoxide is about 87.3%.

Comparative Example 1

The vertical bubble reactor in Example 1 was bypassed, that is, an ethylbenzene reaction liquid containing 0.02 wt % of ethylbenzene hydroperoxide directly entered the first compartment of the horizontal bubble reactor through the reaction liquid inlet 18 of the horizontal bubble reactor at a flow rate of 1.6 tons/hour and flowed through the subsequent three compartments in sequence. With the remaining conditions being the same as those in Example 1, the experiment in Example 1 was repeated.

Under these conditions, a reaction liquid mixture with an ethylbenzene hydroperoxide content of about 7.1 wt % can be obtained at the liquid phase outlet of the reactor and the selectivity of ethylbenzene hydroperoxide is about 87.4%.

Therefore, although the reactor used in Example 1 has a same volume as the reactor used in Comparative Example 1, the reactor combination used in Example 1 can obtain a higher reaction conversion than Comparative Example 1, without a significant difference in selectivity.

Example 2

The diameter of the flow guide cylinder in Example 1 was changed to 0.5 m and its height was 1.0 m, the porosity of the gas distributor in the horizontal bubble reactor was changed to 10%, and then the experiment in Example 1 was repeated. The temperature of the vertical bubble reactor was controlled at 138° C.; in the horizontal bubble reactor, the reaction temperature of the second compartment was 136° C., the reaction temperature of the third compartment was 135° C., and the reaction temperature of the fourth compartment was 134° C.; and the gas phase spaces of the reactors had a pressure of about 3.5 barG.

Under the preceding conditions of the experiment, a reaction liquid mixture with an ethylbenzene hydroperoxide content of about 7.3 wt % can be obtained at the liquid phase outlet of the reactor. The concentration of ethylbenzene hydroperoxide at the outlet of the vertical bubble reactor is about 1.33% and the selectivity of ethylbenzene hydroperoxide is about 88.4%.

Comparative Example 2

The vertical bubble reactor in Example 2 was bypassed, that is, an ethylbenzene reaction liquid containing 0.02 wt % of ethylbenzene hydroperoxide directly entered the first compartment of the horizontal bubble reactor through the reaction liquid inlet 18 of the horizontal bubble reactor at a flow rate of 1.6 tons/hour and flowed through the subsequent three compartments in sequence. With the remaining conditions being the same as those in Example 2, the experiment in Example 2 was repeated.

Under these conditions, a reaction liquid mixture with an ethylbenzene hydroperoxide content of about 6.9 wt % can be obtained at the liquid phase outlet of the reactor and the selectivity of ethylbenzene hydroperoxide is about 88.3%.

Therefore, although the reactor used in Example 2 has a same volume as the reactor used in Comparative Example 2, the reactor combination used in Example 2 can obtain a higher reaction conversion than Comparative Example 2, without a significant difference in selectivity.

Example 3

The reactors used here had the same structures as those in Example 1. In this example, the liquid phase flowing out of the vertical reactor directly entered the first compartment of the horizontal reactor and then flowed through the second, third, and fourth compartments in sequence. In this example, the total residence time was maintained the same as that in Example 1 by adjusting liquid levels in the reactors. With other reaction conditions being the same as those in Example 1, the experiment of Example 1 was repeated.

Under the preceding conditions, a reaction liquid mixture with an ethylbenzene hydroperoxide content of about 7.2 wt % can be obtained at the liquid phase outlet of the reactor. The concentration of ethylbenzene hydroperoxide at the outlet of the vertical bubble reactor is about 1.21% and the total selectivity of ethylbenzene hydroperoxide is about 88.7%.

Comparative Example 3

The reactors used here had the same structures as those in Example 3, the liquid residence time in the vertical reactor was decreased to 30% of the liquid residence time in the vertical reactor in Example 3, and the liquid level in the horizontal reactor was appropriately increased, so as to ensure that the total liquid residence time was the same as that in Example 3. The experiment of Example 3 was repeated under the preceding conditions.

Under the preceding conditions, the content of ethylbenzene hydroperoxide at the liquid phase outlet of the reactor is about 6.77 wt %, the selectivity of ethylbenzene hydroperoxide is about 88.9%, and the concentration of ethylbenzene hydroperoxide at the outlet of the vertical bubble reactor is 0.21 wt %.

A comparison between Example 3 and Comparative Example 3 shows that under the same reaction conditions, when the concentration of ethylbenzene hydroperoxide at the outlet of the vertical bubble reactor is reduced to 0.21 wt %, the selectivity of ethylbenzene hydroperoxide is slightly increased (from 88.7% to 88.9%), but the concentration of ethylbenzene hydroperoxide is reduced relatively greatly (from 7.2 wt % to 6.9 wt %), resulting in reduced production capacity of the reactors.

Comparative Example 4

The reactors used here had the same structures as those in Example 3, the liquid residence time in the vertical reactor was increased to 120% of the liquid residence time in the vertical reactor in Example 3, and the liquid level in the horizontal reactor was appropriately decreased, so as to ensure that the total liquid residence time was the same as that in Example 3. The experiment of Example 3 was repeated under the preceding conditions.

Under the preceding conditions, the content of ethylbenzene hydroperoxide at the liquid phase outlet of the reactor is about 7.4 wt %, the selectivity of ethylbenzene hydroperoxide is about 86.1%, and the concentration of ethylbenzene hydroperoxide at the outlet of the vertical bubble reactor is 2.0 wt %.

A comparison between Example 3 and Comparative Example 4 shows that under the same reaction conditions, when the concentration of ethylbenzene hydroperoxide at the outlet of the vertical bubble reactor is increased to 2.0 wt %, the concentration of ethylbenzene hydroperoxide is increased (from 7.2 wt % to 7.4 wt %), but the selectivity of ethylbenzene hydroperoxide is greatly reduced (from 88.7% to 86.1%), resulting in the generation of a large number of low added values and reduced the economy of the device.

Example 4

The reactors used here had the same structures as those in Example 2. In this example, the liquid phase flowing out of the vertical reactor directly entered the first compartment of the horizontal reactor and then flowed through the second, third, and fourth compartments in sequence. The temperature of the vertical bubble reactor was controlled at 138° C.; in the horizontal bubble reactor, the reaction temperature of the first compartment was 137° C., the reaction temperature of the second compartment was 136° C., the reaction temperature of the third compartment was 135° C., and the reaction temperature of the fourth compartment was 134° C.; and the gas phase spaces of the reactors had a pressure of about 3.5 barG. The liquid levels in each reaction region were maintained the same as those in Example 2, so the liquid phase residence time in this example was increased by about 25% compared with that in Example 2.

Under the preceding conditions of the experiment, a reaction liquid mixture with an ethylbenzene hydroperoxide content of about 8.6 wt % can be obtained at the liquid phase outlet of the reactor. The concentration of ethylbenzene hydroperoxide at the outlet of the vertical bubble reactor is about 1.4% and the selectivity of ethylbenzene hydroperoxide is about 86.9%.

What is claimed is:

1. A method for oxidizing an organic substance, comprising using a device for preparing ethylbenzene hydroperoxide by contacting ethylbenzene with an oxygen-containing gas;
   wherein the device for oxidizing an organic substance comprises a vertical bubble reactor and a horizontal bubble reactor, wherein the horizontal bubble reactor is connected to a reaction product outlet of the vertical bubble reactor and internally provided with a plurality of reaction compartments arranged along the axial direction of the horizontal bubble reactor, and a liquid phase channel is provided between adjacent reaction compartments;
   wherein the concentration of ethylbenzene hydroperoxide at the outlet of the vertical bubble reactor is controlled at 0.5%-1.5%.

2. The method according to claim 1, wherein in a case where ethylbenzene hydroperoxide with a concentration of C is obtained at the reaction liquid outlet of the horizontal bubble reactor comprising N reaction compartments, the concentration of ethylbenzene hydroperoxide at the outlet of the vertical bubble reactor is controlled at 80%-95% of $$\frac{C}{N+1}.$$

3. The method according to claim 1, wherein the concentration of ethylbenzene hydroperoxide at the outlet of the vertical bubble reactor is controlled at 1%-1.5%.

* * * * *